(12) United States Patent
Iitsuka et al.

(10) Patent No.: US 11,844,762 B2
(45) Date of Patent: Dec. 19, 2023

(54) FAT ABSORPTION INHIBITING AGENT, FOOD AND DEFATTED SESAME SEEDS, AND METHOD FOR INHIBITING OBESITY

(71) Applicants: Pharma Foods International Co., Ltd., Kyoto (JP); Mitsui DM Sugar Co., Ltd., Tokyo (JP)

(72) Inventors: Hiroaki Iitsuka, Kyoto (JP); Sayo Morita, Kyoto (JP); Keita Koga, Kyoto (JP); Atsushi Yamatsu, Kyoto (JP); Mujo Kim, Kyoto (JP); Toma Furuta, Tokyo (JP)

(73) Assignees: Pharma Foods International Co.. Ltd., Kyoto (JP); Mitsui DM Sugar Co., Ltd., Tokyo (JP)

(*) Notice: Subject to any disclaimer, the term of this patent is extended or adjusted under 35 U.S.C. 154(b) by 261 days.

(21) Appl. No.: 17/183,646

(22) Filed: Feb. 24, 2021

(65) Prior Publication Data
US 2021/0268053 A1 Sep. 2, 2021

(30) Foreign Application Priority Data
Feb. 25, 2020 (JP) ................. 2020-029647

(51) Int. Cl.
| A61K 36/185 | (2006.01) |
| A61P 3/04 | (2006.01) |
| A23L 33/00 | (2016.01) |
| A23L 25/00 | (2016.01) |
| A23K 10/30 | (2016.01) |
| A23L 33/105 | (2016.01) |

(52) U.S. Cl.
CPC ............ *A61K 36/185* (2013.01); *A23K 10/30* (2016.05); *A23L 25/30* (2016.08); *A23L 33/105* (2016.08); *A23L 33/40* (2016.08); *A61P 3/04* (2018.01); *A23V 2002/00* (2013.01)

(58) Field of Classification Search
None
See application file for complete search history.

(56) References Cited

FOREIGN PATENT DOCUMENTS

| JP | 2005-289951 A | 10/2005 |
| JP | 2006-169181 A | 6/2006 |
| JP | 2010-209051 A | 9/2010 |
| JP | 2014-172901 A | 9/2014 |
| WO | WO 2005/0997356 A1 | 10/2005 |

OTHER PUBLICATIONS

Iombor et al.(J Nutrition Health Food Sci 4(3):1-7, 2016). (Year: 2016).*
Manikantan et al.(J Food Technol 52(3): 1778-1783, 2015) (Year: 2015).*
Sharma et al.(Food Measure 10:520-526, 2016) (Year: 2016).*

* cited by examiner

*Primary Examiner* — Craig D Ricci
(74) *Attorney, Agent, or Firm* — Knobbe Martens Olson & Bear LLP

(57) ABSTRACT

Problem to be solved: An object of the present invention is to provide a novel fat absorption inhibiting agent.
Solution to the problem: The present invention provides a fat absorption inhibiting agent comprising pulverized defatted sesame seeds or a processed product thereof. The present invention also provides a fat absorption inhibiting agent comprising defatted sesame seeds having a 50th percentile particle size of 1 to 200 μm as determined by laser diffraction/scattering and a compressibility index of 30 to 80%. The fat absorption inhibiting agent of the present invention preferably has lipase inhibitory activity. The present invention also provides a food comprising the agent. The present invention also provides defatted sesame seeds having a 50th percentile particle size of 1 to 200 μm as determined by laser diffraction/scattering and a compressibility index of 30 to 80%. The present invention provides a method for inhibiting obesity in a human or animal, the method comprising administering to a human or animal the agent, the food or the defatted sesame seeds.

7 Claims, 3 Drawing Sheets

FAT ABSORPTION INHIBITING AGENT, FOOD AND DEFATTED SESAME SEEDS, AND METHOD FOR INHIBITING OBESITY

TECHNICAL FIELD

The present invention relates to a fat absorption inhibiting agent, a food and defatted sesame seeds, and a method for inhibiting obesity.

BACKGROUND ART

The obese population is increasing in the world due to changes in eating habits, lifestyle, etc. Obesity is a risk factor that increases various health risks, including diabetes mellitus, hypertension and cancer. It is estimated that, around the world, 4 million people die from obesity-associated diseases annually.

Currently available anti-obesity drugs include (1) drugs acting on the appetite center to suppress appetite (Mazindol etc.), and (2) drugs inhibiting intestinal lipase to inhibit absorption of fats (Orlistat etc.). Many of these anti-obesity drugs have some adverse side effects, and their safety still has not been well established. There only are a few anti-obesity drugs that can be used for a long period of time.

Under these circumstances, the fat absorption inhibiting agents inhibiting lipase activity as described in the above (2) have been investigated to develop new drugs with higher safety using food materials. Some food materials are known to inhibit lipase activity, including *Eucommia* leaves (Patent literature 1), *Pulsatillae radix*, the flower buds and inflorescences of *Buddleja officinalis*, *Erythrina indica* bark, oriental arborvitae kernel, *Benincasa* seed (Patent literature 2), black ginger, red ginger, cinnamon tree, barley young leaves, black garlic, powdered gambir, hydrangea, myrobalan fruit, pomegranate, *Linum usitatissimum* seed, the flowers of *Osmanthus fragrans* var. *aurantiacus, Sarcandra glabra* tea, *Saxifraga stolonifera*, jasmine tea, oregano, olive leaves, sea buckthorn, curry leaves (Patent literature 3), and *Psychotria serpens* L. (Patent literature 4).

CITATION LIST

Patent Literature

Patent literature 1: JP 2005-289951 A
Patent literature 2: JP 2006-169181 A
Patent literature 3: JP 2010-209051 A
Patent literature 4: JP 2014-172901 A

SUMMARY OF INVENTION

Technical Problem

The market supply of the food materials as described above is, however, often small, and results in increase in the cost and reduction in the distribution of the products.

For easy availability and cost reduction etc., a fat absorption inhibiting agent produced from a more common food material has been desired.

The present invention has been made under these circumstances, and an object of the invention is to provide a novel fat absorption inhibiting agent.

Solution to Problem

The inventors conducted extensive studies to solve the above problems, and found that pulverized defatted sesame seeds show fat absorption inhibitory effect. The inventors performed further studies based on this finding, and completed the invention.

A first aspect of the invention for solving the above problems is directed to a fat absorption inhibiting agent comprising pulverized defatted sesame seeds or a processed product thereof.

Another aspect of the invention for solving the above problems is directed to a fat absorption inhibiting agent comprising defatted sesame seeds having a 50th percentile particle size of 1 to 200 μm as determined by laser diffraction/scattering and a compressibility index of 30 to 80%.

A further another aspect of the invention for solving the above problems is directed to defatted sesame seeds having a 50th percentile particle size of 1 to 200 μm as determined by laser diffraction/scattering and a compressibility index of 30 to 80%.

A further another aspect of the invention for solving the above problems is directed to a method for inhibiting obesity in a human or animal, the method comprising administering to a human or animal the agent, a food according to the invention or the defatted sesame seeds.

In particular, the present invention relates to the following.

(1) A fat absorption inhibiting agent comprising pulverized defatted sesame seeds or a processed product thereof.
(2) A fat absorption inhibiting agent comprising defatted sesame seeds having a 50th percentile particle size of 1 to 200 μm as determined by laser diffraction/scattering and a compressibility index of 30 to 80%.
(3) The agent according to the above (1) or (2), which has lipase inhibitory activity.
(4) A food comprising the agent according to any one of the above (1) to (3).
(5) Defatted sesame seeds having a 50th percentile particle size of 1 to 200 μm as determined by laser diffraction/scattering and a compressibility index of 30 to 80%.
(6) A method for inhibiting obesity in a human or animal, the method comprising administering to a human or animal the agent according to any one of the above (1) to (3), the food according to the above (4) or the defatted sesame seeds according to the above (5).

Advantageous Effects of Invention

The present invention provides a novel fat absorption inhibiting agent. The fat absorption inhibiting agent of the present invention is produced from a food material, and is therefore highly safe. The fat absorption inhibiting agent of the present invention has excellent fat absorption inhibitory activity and excellent lipase inhibitory activity. The fat absorption inhibiting agent of the present invention is easy to produce without requiring complicated production procedures. The food of the present invention comprises the fat absorption inhibiting agent of the present invention and therefore has fat absorption inhibitory activity and lipase inhibitory activity. The defatted sesame seeds of the present invention can be appropriately used as an ingredient of the fat absorption inhibiting agent of the present invention. The agent, food, and defatted sesame seeds of the present invention can therefore be administered to a human or animal to inhibit obesity of the human or animal. The present invention can be appropriately applied to pharmaceutical products, foods, food additives, functional foods, etc. for treating or preventing obesity, diseases caused by accumulation of fats, such as serum hypertriglyceridemia, or diseases caused by obesity, such as diabetes mellitus, hyperlipemia, hypertension and arteriosclerosis, or for dieting.

DESCRIPTION OF EMBODIMENTS

Fat Absorption Inhibiting Agent

Figure 1:
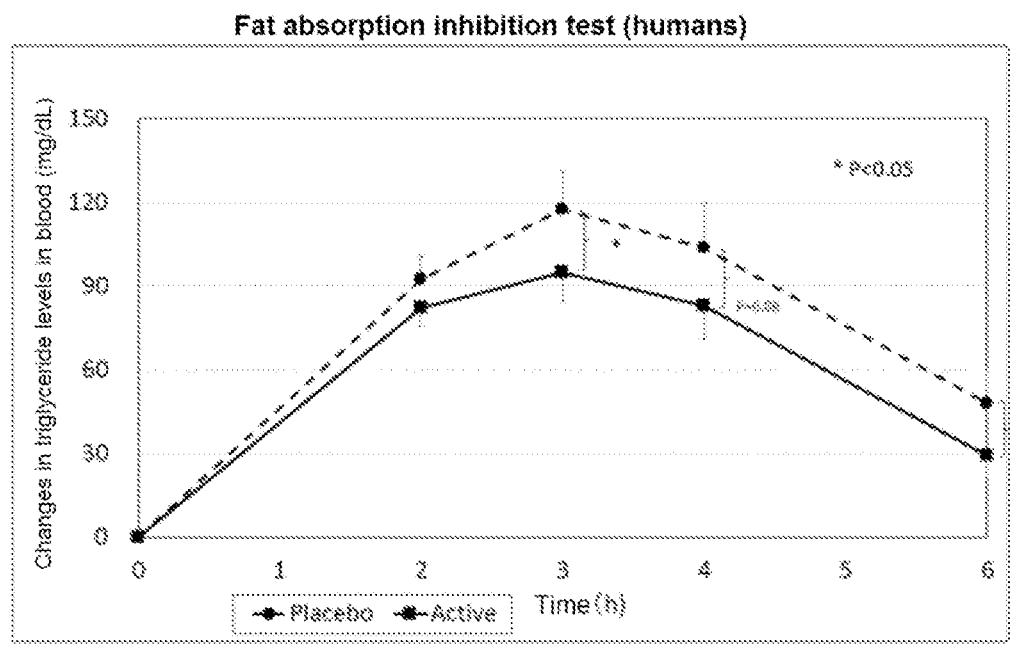
FIG. 1 is a graph showing the results of a fat absorption inhibition test (in humans).

The fat absorption inhibiting agent comprises an ingredient having the effect of inhibiting transport of lipids, such as neutral fat (triglyceride), into the blood (fat absorption inhibitory activity). The fat absorption inhibiting agent typically has lipase inhibitory activity.

Aspects of the fat absorption inhibiting agent of the present invention include the following (1) to (4):

(1) a fat absorption inhibiting agent comprising pulverized defatted sesame seeds or a processed product thereof;

(2) a fat absorption inhibiting agent comprising defatted sesame seeds having a 50th percentile particle size of 1 to 200 μm as determined by laser diffraction/scattering;

(3) a fat absorption inhibiting agent comprising defatted sesame seeds having a compressibility index of 30 to 80%; and (4) a fat absorption inhibiting agent comprising defatted sesame seeds having a 50th percentile particle size of 1 to 200 μm as determined by laser diffraction/scattering and a compressibility index of 30 to 80%.

The fat absorption inhibiting agent comprises as an essential ingredient "pulverized defatted sesame seeds or a processed product thereof," and preferably comprises "defatted sesame seeds having a 50th percentile particle size of 1 to 200 μm as determined by laser diffraction/scattering and a compressibility index of 30 to 80%". The fat absorption inhibiting agent of the present invention may further comprise another ingredient to the extent that it does not impair the effects of the present invention. The ingredients contained in the agent will be described in detail below.

Pulverized Defatted Sesame Seeds or a Processed Product Thereof

The fat absorption inhibiting agent according an aspect of the present invention comprises pulverized defatted sesame seeds or a processed product thereof.

Typically, the pulverized defatted sesame seeds are preferably produced by pulverizing defatted sesame seeds (non-powdered form) to a finer powder than a "powdered form" with a reduced particle size. The mean particle size of the pulverized defatted sesame seeds is preferably a half or less than a half of the particle size of non-powdered sesame seeds, and is more preferably a quarter or less than a quarter of the particle size of non-powdered sesame seeds. The mean particle size of the pulverized defatted sesame seeds in terms of a 50th percentile particle size is especially preferably, for example, 200 μm or less.

The "processed product" of the pulverized defatted sesame seeds refers to a product obtained by mechanical processing and/or chemical processing of the pulverized defatted sesame seeds. Examples of the processed product of the pulverized defatted sesame seeds include an extract obtained by extraction of the pulverized defatted sesame seeds, a concentrate of the extract, the residual pulverized seeds, a dried product and a frozen product.

The extraction solvent for the extraction may be, for example, alcohols such as ethanol and aqueous ethanol solution, ketones such as acetone, ethers such as diethyl ether, esters such as ethyl acetate, hydrocarbons such as toluene, or the like. The extraction temperature is preferably at least 0° C., more preferably at least 20° C. The extraction temperature is preferably up to 100° C., more preferably up to 70° C. The extraction time is preferably at least 10 seconds, more preferably at least 1 minute. The extraction time is preferably up to 5 hours, more preferably up to 1 hour. The mass ratio of the extraction solvent and the pulverized defatted sesame seeds (extraction solvent/pulverized defatted sesame seeds) in the extraction is preferably at least 0.1, more preferably at least 1. The mass ratio (extraction solvent/pulverized defatted sesame seeds) is preferably up to 100, more preferably up to 10.

The disclosure of the present invention includes any combination of the minimum and maximum values described above.

The extract obtained by the extraction may be processed to produce a concentrate by, for example, concentration under atmospheric pressure, vacuum concentration, etc.

Defatted Sesame Seeds

The inventors found that defatted sesame seeds have no fat absorption inhibitory activity before pulverization, but once pulverized, defatted sesame seeds exhibit fat absorption inhibitory activity.

The term "defatted sesame seeds" means a defatted sesame seed ingredient.

Examples of the sesame seed ingredient include black sesame seeds, white sesame seeds and golden sesame seeds. The sesame seed ingredient may be roasted sesame seeds. Roasting of the sesame seed ingredient may be performed in accordance with a known method.

Defatting of the sesame seed ingredient may be performed by, for example, press extraction method, solvent extraction method, such as hexane extraction method, etc. Defatting of the sesame seed ingredient may be performed in accordance with a known method.

The defatted sesame seeds (non-powdered form) may be, for example, common defatted sesame seeds that are distributed in the market and have a fat content of 35% by mass or less. Examples of commercially available defatted sesame seeds (non-powdered form) include "Goma Abura kasu" manufactured by Pollars Laboratory Corporation.

The fat content of the defatted sesame seeds (non-powdered form) is preferably up to 35% by mass, more preferably up to 30% by mass, further more preferably up to 25% by mass, especially preferably up to 15% by mass. The fat content of the defatted sesame seeds (non-powdered form) is preferably at least 1% by mass, more preferably at least 2% by mass, further more preferably at least 5% by mass, especially preferably at least 8% by mass.

The mean particle size of the defatted sesame seeds (non-powdered form) in terms of a 50th percentile particle size is not limited to a specific value, but is typically 250 μm to 3 mm, preferably 300 μm to 1 mm, more preferably 400 to 800 μm.

The pulverized defatted sesame seeds may be produced by pulverizing the defatted sesame seeds (non-powdered form) using, for example, a pulverizing mill, such as a ball mill, a tube mill, a jet mill, a hammer mill, a grinding mill, a pin mill, an air-swept mill, a disc mill, a vibration mill, a stone mill, and a planetary mill.

The temperature during pulverization of the defatted sesame seeds is preferably at least −30° C., more preferably at least 0° C. The temperature during pulverization of the defatted sesame seeds is preferably up to 100° C., more preferably up to 50° C. The duration of pulverization of the defatted sesame seeds is preferably at least 10 seconds, more preferably at least 1 minute. The duration of pulverization of the defatted sesame seeds is preferably up to 5 hours, more preferably up to 1 hour.

A fat absorption inhibiting agent according to another aspect of the present invention comprises defatted sesame seeds having a 50th percentile particle size of 1 to 200 μm as determined by laser diffraction/scattering. If the 50th percentile particle size of the defatted sesame seeds exceeds the higher end of the above range, fat absorption inhibitory activity will be low and insufficient. On the other hand, if the 50th percentile particle size of the defatted sesame seeds falls short of the lower end of the above range, the fluidity will be significantly reduced and good handling will not be achieved.

The 50th percentile particle size of the defatted sesame seeds contained in the fat absorption inhibiting agent is preferably at least 1 μm, more preferably at least 10 μm, further more preferably at least 20 μm, especially preferably at least 40 μm. The 50th percentile particle size of the defatted sesame seeds is preferably up to 200 μm, more preferably up to 180 μm, further more preferably up to 160 μm, especially preferably up to 140 μm. The fat absorption inhibiting agent comprising such defatted sesame seeds having a 50th percentile particle size within the above range shows enhanced fat absorption inhibitory activity.

The "50th percentile particle size as determined by laser diffraction/scattering" herein is determined using, for example, a laser diffraction particle size distribution analyzer (such as SALD-2200 by Shimadzu Corporation and Mastersizer 3000 by Malvern Instruments Limited) by precisely following the measurement procedures described in the manufacturer's instructions of the analyzer. The term "50th percentile particle size" means the "median particle diameter (D50)."

A fat absorption inhibiting agent according to another aspect of the present invention comprises defatted sesame seeds having a compressibility index of 30 to 80%. If the compressibility index of the defatted sesame seeds exceeds the higher end of the above range, the fluidity will be significantly reduced and good handling will not be achieved. On the other hand, if the compressibility index of the defatted sesame seeds falls short of the lower end of the above range, fat absorption inhibitory activity will be low and insufficient.

The compressibility index of the defatted sesame seeds contained in the fat absorption inhibiting agent is preferably at least 30%, more preferably at least 35%, further more preferably at least 40%, especially preferably at least 45%. The compressibility index of the defatted sesame seeds is preferably up to 80%, more preferably up to 75%, further more preferably up to 70%, especially preferably up to 65%. The fat absorption inhibiting agent comprising such defatted sesame seeds having a compressibility index within the above range shows enhanced fat absorption inhibitory activity.

The "compressibility index" herein is determined, for example, as follows. First, the "tapped bulk density" and the "loose bulk density" are measured on a multifunctional powder physical properties analyzer (such as Multi Tester MT-02, Seishin Enterprise Co., Ltd.) by precisely following the measurement procedures described in the manufacturer's instructions of the analyzer. The compressibility index is then calculated from the measured values by the following formula:

Compressibility index (%)=(tapped bulk density (g/mL)−loose bulk density (g/mL))/tapped bulk density (g/mL)×100.

The tapped bulk density of the defatted sesame seeds is preferably at least 0.50 g/mL, more preferably at least 0.55 g/mL. The tapped bulk density of the defatted sesame seeds is preferably up to 0.62 g/mL, more preferably up to 0.60 g/mL.

The loose bulk density of the defatted sesame seeds is preferably at least 0.20 g/mL, more preferably at least 0.25 g/mL. The loose bulk density of the defatted sesame seeds is preferably up to 0.40 g/mL, more preferably up to 0.35 g/mL.

The working bulk density of the defatted sesame seeds is preferably at least 0.35 g/mL, more preferably at least 0.40 g/mL. The working bulk density of the defatted sesame seeds is preferably up to 0.60 g/mL, more preferably up to 0.55 g/mL.

The angle of repose of the defatted sesame seeds is preferably at least 35°, more preferably at least 40°. The angle of repose of the defatted sesame seeds is preferably up to 60°, more preferably up to 55°.

The angle of collapse of the defatted sesame seeds is preferably at least 15°, more preferably at least 20°. The angle of collapse of the defatted sesame seeds is preferably up to 30°, more preferably up to 27°.

The angle of difference (as determined by deducting the angle of collapse from the angle of repose) of the defatted sesame seeds is preferably at least 15°, more preferably at least 20°. The angle of difference of the defatted sesame seeds is preferably up to 30°, more preferably up to 25°.

The angle of spatula of the defatted sesame seeds is preferably at least 55°, more preferably at least 60°. The angle of spatula of the defatted sesame seeds is preferably up to 75°, more preferably up to 70°.

A fat absorption inhibiting agent according to another aspect of the present invention comprises defatted sesame seeds having a 50th percentile particle size of 1 to 200 μm as determined by laser diffraction/scattering and a compressibility index of 30 to 80%.

The fat absorption inhibiting agent comprising such defatted sesame seeds having a 50th percentile particle size and a compressibility index within the above ranges shows higher fat absorption inhibitory activity.

Other Ingredients

Examples of other ingredients that may be contained in the fat absorption inhibiting agent include carbohydrate sweeteners (monosaccharides such as fructose, glucose, tagatose and arabinose; oligosaccharides such as lactose, oligosaccharide, trehalose and maltose; powdered starch syrup; dextrin; sugar alcohol; etc.), high-intensity sweeteners (sucralose, acesulfame K, *stevia*, etc.), polysaccharides such as starch, flavor improvers such as vanillin, flavor ingredients (egg, coffee, tea, cocoa, fruit juice, fruit flesh, yogurt, liquor, etc.), amino acids, proteins, dietary fiber, vitamins, minerals, acidulants, fragrances, fats and oils, dairy products, excipients, preservatives, dyes, acidulants, emulsifiers and agar.

These ingredients can be used alone or in combination of two or more types.

The fat absorption inhibiting agent may be in various forms, such as a powder, granules, a paste or a suspension. Such a formulation containing the fat absorption inhibiting agent and a method for producing the same are well established in the art, and the formulation of the present invention may be produced in accordance with such a well-established method.

The timing of ingestion of the fat absorption inhibiting agent is not limited to a particular one, and, for example, the fat absorption inhibiting agent may be ingested before or after or simultaneously with a meal. The fat absorption inhibiting agent is preferably ingested simultaneously with a meal to achieve efficient fat absorption inhibitory effect.

When the fat absorption inhibiting agent is ingested before or after or simultaneously with a meal, the dose of the fat absorption inhibiting agent per meal in terms of the amount of the pulverized defatted sesame seeds is preferably at least 50 mg, more preferably at least 100 mg. The dose of the fat absorption inhibiting agent per meal is preferably up to 10 g, more preferably up to 1 g.

The fat absorption inhibiting agent can be applied to various types of foods as well as pharmaceutical products or common industrial products. The fat absorption inhibiting agent is especially suitable for application to foods in that the fat absorption inhibiting agent can be easily and enjoyably taken to exhibit fat absorption inhibitory activity in a convenient and efficient manner.

Foods

A food of the present invention comprises the fat absorption inhibiting agent as described above. Addition of the fat absorption inhibiting agent to a food may be performed by a technique known in the art.

Examples of the food include sweets (chewing gums, candies, tablet candies, chocolates, jellies, etc.), frozen desserts, carbonated foods such as noodles, bakery foods (bread, biscuits, etc.), fat and oily foods (margarine, shortening, fat-spread, etc.), dairy products (butter, cream, cheese, etc.), drinks (juice, tea, energy drink, etc.), seasonings (soy sauce, sugar, miso, sweet cooking sake (Mirin), dressing, dipping sauce, etc.), and dietary supplements (proteins, tablet candies, pills, capsules, tablets, powders, granules, etc.). In a preferred embodiment, the fat absorption inhibiting agent is added to dietary supplements, noodles, bread, or batter for deep-fried foods.

The amount of the fat absorption inhibiting agent contained in the food varies depending on the type of the food, the purpose of the ingestion, etc., but the amount of the fat absorption inhibiting agent contained in the food in terms of the amount of the pulverized defatted sesame seeds is preferably at least 0.0001% by mass, more preferably at least 0.01% by mass, further more preferably at least 1% by mass, especially preferably at least 10% by mass. The amount of the fat absorption inhibiting agent contained in the food may be up to 100% by mass.

EXAMPLES

The present invention will be described in more detail below with reference to Examples, but the present invention is not limited thereto.

Production Example 1: Production of Fat Absorption Inhibiting Agent (A)

Defatted sesame seeds (Defatted sesame seed powder, Mitsui & Co., Ltd.) were pulverized with a hammer mill (ACM30, Hosokawa Micron Corporation) at a rotational speed of 3000 rpm to produce pulverized defatted sesame seeds. The resulting pulverized defatted sesame seeds were used as a fat absorption inhibiting agent (A).

Test Example 1: Determination of 50th Percentile Particle Size and Compressibility Index Determination of 50th Percentile Particle Size The particle size distribution of the defatted sesame seeds (non-powdered form) was determined with a laser diffraction particle size distribution analyzer (SALD-2200, Shimadzu Corporation).

The particle size distribution of the defatted sesame seeds (non-powdered form) was measured at three different positions in the defatted sesame seed sample, and the 50th percentile particle size (D50, median particle diameter) was determined to be 278 μm, 457 μm and 567 μm.

The particle size distribution of the fat absorption inhibiting agent (A) was determined with a laser diffraction particle size distribution analyzer (Mastersizer 3000, Malvern Instruments Limited).

The particle size distribution of the fat absorption inhibiting agent (A) was measured three times, and the 50th percentile particle size (D50, median particle diameter) was determined to be 32.7 μm, 30.7 μm and 32.0 μm.

Determination of Compressibility Index

The compressibility index of the defatted sesame seeds (non-powdered form) and the fat absorption inhibiting agent (A) was determined using a multifunctional powder physical properties analyzer (Multi Tester MT-02, Seishin Enterprise Co., Ltd.). The compressibility index was calculated from the measured values of the tapped bulk density and the loose bulk density using the calculation formula for the compressibility index as shown below.

Calculation Formula for Compressibility Index

Compressibility index (%)=(tapped bulk density (g/mL)−loose bulk density (g/mL))/tapped bulk density (g/mL)×100

Table 1 below shows the measured values (loose bulk density, tapped bulk density, working bulk density, angle of repose, angle of collapse, and angle of spatula) and the calculated values of the compressibility index and the angle of difference for the defatted sesame seeds (non-powdered form) and the fat absorption inhibiting agent (A).

TABLE 1

| Name | Angle of repose (°) | Angle of collapse (°) | Angle of difference (°) | Angle of spatula (°) | Loose bulk density (g/mL) | Tapped bulk density (g/mL) | Working bulk density (g/mL) | Compressibility index (%) |
|---|---|---|---|---|---|---|---|---|
| Defatted sesame seeds | 43.9 | 31.0 | 12.9 | — | 0.488 | 0.637 | 0.523 | 23.4 |
| | 38.7 | 31.0 | 7.7 | 51.35 | 0.499 | 0.629 | 0.526 | 20.7 |
| | 43.2 | 33.1 | 10.1 | 51.9 | 0.508 | 0.627 | 0.531 | 19.0 |

TABLE 1-continued

| Name | Angle of repose (°) | Angle of collapse (°) | Angle of difference (°) | Angle of spatula (°) | Loose bulk density (g/mL) | Tapped bulk density (g/mL) | Working bulk density (g/mL) | Compressibility index (%) |
|---|---|---|---|---|---|---|---|---|
| (non-powdered form) | 39.1 | 26.9 | 12.2 | 52 | — | — | — | — |
|  | 39.3 | 26.9 | 12.4 | 52.2 | — | — | — | — |
| Fat absorption inhibiting agent (A) | 52.5 | 26.0 | 26.5 | 54.6 | 0.269 | 0.587 | 0.441 | 54.2 |
|  | 50.7 | 27.3 | 23.4 | 63.9 | 0.277 | 0.584 | 0.438 | 52.6 |
|  | 50.6 | 29.1 | 21.5 | 65.65 | 0.272 | 0.589 | 0.443 | 53.8 |
|  | 42.9 | 22.5 | 20.4 | 65.05 | — | — | — | — |
|  | 45.9 | 26.4 | 19.5 | — | — | — | — | — |

The compressibility index of the defatted sesame seeds (non-powdered form) was measured at three different positions in the defatted sesame seed sample and determined to be 19.0%, 20.7% and 23.4%.

The compressibility index of the fat absorption inhibiting agent (A) was measured at three different positions in the agent sample and determined to be 52.6%, 53.8% and 54.2%.

Production Example 2: Production of Fat Absorption Inhibiting Agent (B)

Fifty grams of the fat absorption inhibiting agent (A) produced in Production Example 1 was subjected to extraction with 500 mL of 50 vol % aqueous ethanol solution at 30° C. for 180 minutes. The extract liquid was concentrated in vacuum to produce 7.7 g of a fat absorption inhibiting agent (B).

Test Example 2: Fat Absorption Inhibition Test (in Humans)

Fat absorption inhibition test in humans using the fat absorption inhibiting agent (B) was performed as follows.

Twenty-six healthy male and female subjects aged at 22 years or older and less than 56 years were divided into two groups of 13 persons each: Active group and Placebo group.

The Active group ingested test food 1 as shown in Table 2 below, and immediately after that, ingested high-fat meals (total lipid content: 41.2 g) as shown in Table 3.

The Placebo group ingested test food 2 as shown in Table 2 below, and immediately after that, ingested the same meals as those ingested by the Active group.

The blood was collected at 0, 2, 3, 4 and 6 hours after ingestion of the high-fat meals, and the triglyceride levels in the blood were measured. The changes in the triglyceride levels in the blood [mg/dL] were calculated from the measured values of the triglyceride levels in the blood at each of the time points using the calculation formula for changes in the triglyceride levels in the blood as shown below.

Calculation Formula for Changes in Triglyceride Levels in Blood

Changes in triglyceride levels in blood=triglyceride level in blood after ingestion of high-fat meals−triglyceride level in blood before ingestion of high-fat meals The composition of the test foods used in the fat absorption inhibition test (in humans) is shown in Table 2 below.

TABLE 2

| | Form | Composition | Amount |
|---|---|---|---|
| Test food 1 | Powder | Fat absorption inhibiting agent (B) | 90 mg |
| | | Dextrin | 810 mg |
| Test food 2 | Powder | Dextrin | 900 mg |

The details of the high-fat meals used in the fat absorption inhibition test (in humans) are shown in Table 3 below.

TABLE 3

| Product name | Manufacturer | Amount of ingestion | Lipid/calorie |
|---|---|---|---|
| Tasmania Beef Japanese Style Hamburger Steak | TOPVALU | 1 pouch | 17.0 g/288 kcal |
| Neo Butter rolls | FUJI BAKING Group. | 2 pieces | 16.0 g/314 kcal |
| Ohayo potato Hashed potatoes | Heinz Japan | 1 pouch | 8.2 g/135 kcal |
| Total | | | 41.2 g/737 kcal |

The results of Test Example 2 are shown in FIG. 1. The changes in the triglyceride levels in the blood were significantly lower in the Active group than in the Placebo group at 3 and 6 hours after ingestion of the high-fat meals (3 hours after ingestion: P (significance probability)=0.04, 6 hours after ingestion: P=0.01). The results demonstrate that the fat absorption inhibiting agent (B) inhibits fat absorption in humans after ingestion of meals.

Test Example 3: Fat Absorption Inhibition Test (In Vivo) Using Non-Powdered Defatted Sesame Seeds Fat absorption inhibition test in rats using the defatted sesame seeds (non-powdered form) was performed as follows.

An emulsified corn oil as a lipid-loading diet was prepared by mixing 30 mL of corn oil with 400 mg of cholic acid, 10 g of cholesterol oleate and 30 mL of pure water, and ultrasonicating the mixture for 10 minutes to allow for emulsification.

The body weight of rats was measured, and the dose was calculated according to the weight so that the defatted sesame seeds (non-powdered form) were administered at 125 mg/kg of the body weight of rats. The non-powdered defatted sesame seeds used in Production Example 1 were suspended in 20% (v/v) ethanol solution (at 50.9 mg/mL) to produce a test liquid A.

Wister rats (male, 6 weeks old) were divided into two groups: a non-powdered defatted sesame seed group and a control group (7 animals per group). The non-powdered defatted sesame seed group orally received 400 µL of the test liquid A (dose of the defatted sesame seeds (non-powdered form): 20.4 mg (human equivalent dose: about 1 g (based on a body weight of 60 kg))). The control group orally received 400 µL of 20% (v/v) ethanol solution. The both groups then orally received 1 mL of the emulsified corn oil at 10 minutes after the oral administration of the test liquid A or the ethanol solution. The blood was collected every 1.5 hours after administration of the lipid-loading diet until 7.5 hours. The blood was left to stand for 30 minutes, and centrifuged (at 3000×g for 15 minutes). The serum was separated to measure the triglyceride concentration in the blood [mg/mL]. The triglyceride concentration in the blood was measured following the measurement procedure of LabAssay™ Triglyceride (FUJIFILM Wako Pure Chemical Corporation).

Test Example 4: Fat Absorption Inhibition Test (In Vivo) Using Pulverized Defatted Sesame Seeds Fat absorption inhibition test in rats using the fat absorption inhibiting agent (A) was performed as follows.

The body weight of rats was measured, and the dose was calculated according to the weight so that the fat absorption inhibiting agent (A) was administered at 125 mg/kg. The fat absorption inhibiting agent (A) produced in Production Example 1 was suspended in 20% (v/v) ethanol solution (at 45.0 mg/mL) to produce a test liquid B.

Wister rats (male, 6 weeks old) were divided into two groups: a pulverized defatted sesame seed group and a control group (7 animals per group). The pulverized defatted sesame seed group orally received 400 µL of the test liquid B as the fat absorption inhibiting agent (A) (dose: 18.8 mg (human equivalent dose: about 1 g/day)). The control group orally received 400 µL of 20% (v/v) ethanol solution. The both groups then orally received 1 mL of the emulsified corn oil at 10 minutes after the oral administration of the test liquid B or the ethanol solution. The blood was collected every 1.5 hours after administration of the lipid-loading diet until 7.5 hours. The blood was left to stand for 30 minutes, and centrifuged (at 3000×g for 15 minutes). The serum was separated to measure the triglyceride concentration in the blood [mg/mL]. The triglyceride concentration in the blood was measured following the measurement procedure of LabAssay™ Triglyceride (FUJIFILM Wako Pure Chemical Corporation).

Figure 2:
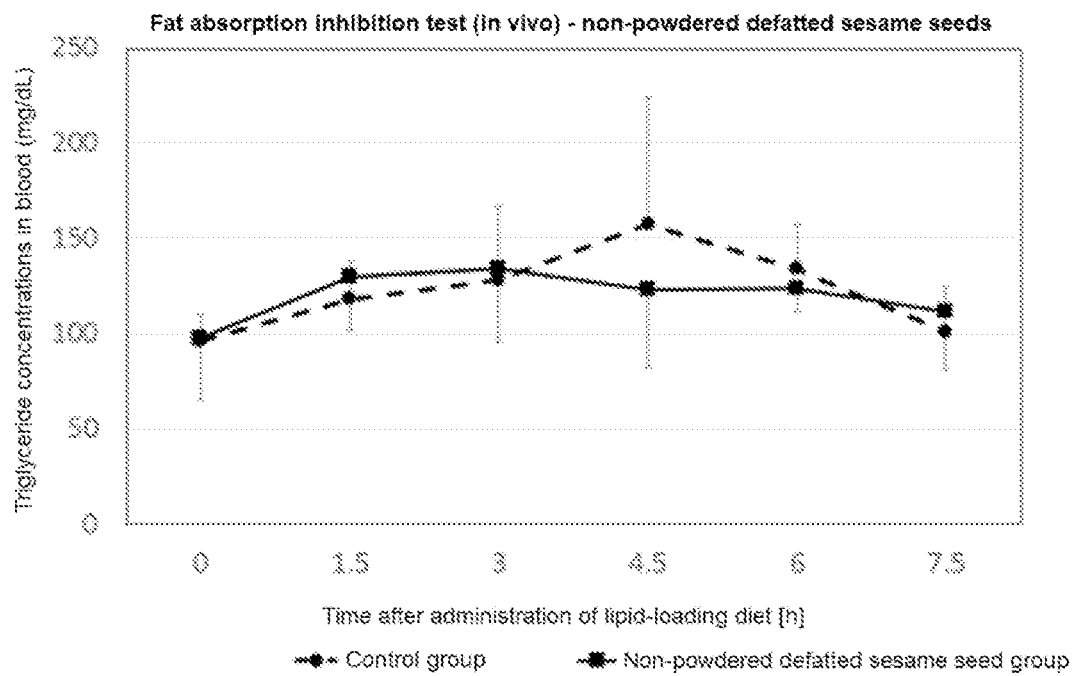
FIG. 2 is a graph showing the results of a fat absorption inhibition test (in vivo) using non-powdered defatted sesame seeds.

The results of Test Example 3 are shown in FIG. 2. During the course of the test example, one subject in the control group developed conditions that prevented the continuation of the test, and was excluded from the group. The non-powdered defatted sesame seeds did not show inhibition of fat absorption.

Figure 3:
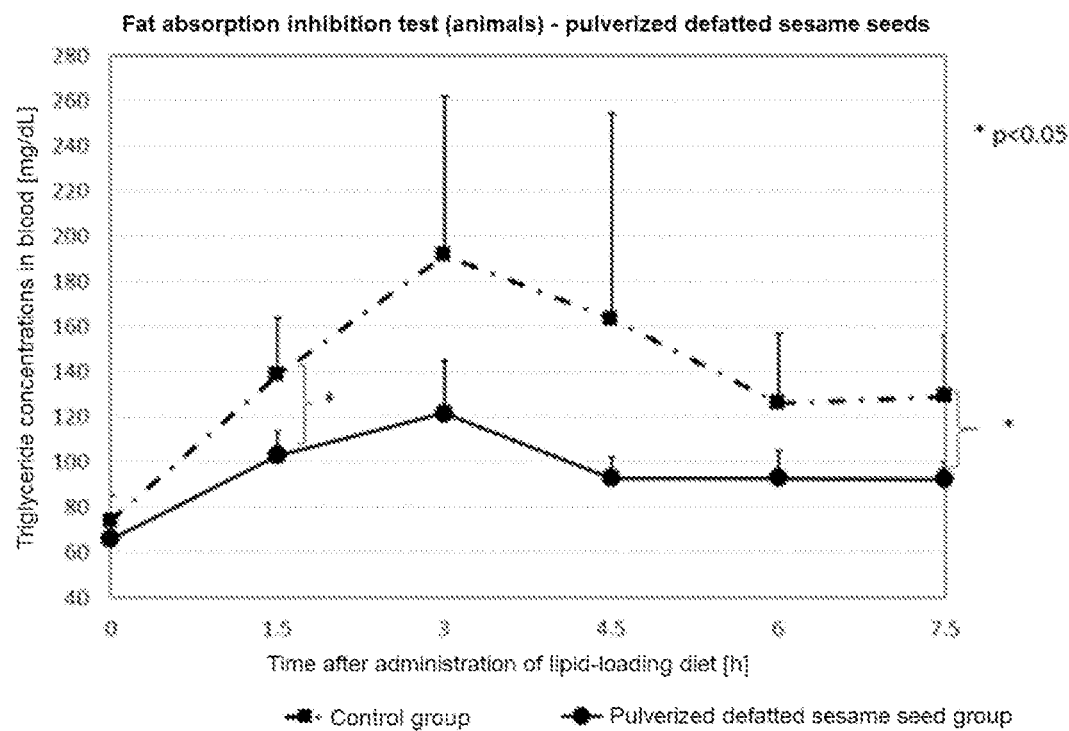
FIG. 3 is a graph showing the results of a fat absorption inhibition test (in vivo) using pulverized defatted sesame seeds.

The results of Test Example 4 are shown in FIG. 3. The triglyceride level in the blood of the pulverized defatted sesame seed group that received the fat absorption inhibiting agent (A) was significantly lower than that of the control group at 1.5 and 7.5 hours after the administration of the lipid-loading diet (1.5 hours after administration: P=0.03, 7.5 hours after administration: P=0.01), demonstrating that the fat absorption inhibiting agent (A) inhibits fat absorption.

The results of Test Examples 3 and 4 demonstrate that pulverization of defatted sesame seeds (non-powdered form) results in induction of lipid absorption inhibitory effect.

Production Example 3: Production of Fat Absorption Inhibiting Agent (C)

Fifty grams of the fat absorption inhibiting agent (A) produced in Production Example 1 was subjected to extraction with 500 mL of 50 vol % aqueous ethanol solution at room temperature for 180 minutes, and the extract liquid was concentrated in vacuum to produce 9 g of a fat absorption inhibiting agent (C).

Test Example 5: Lipase Inhibition Test (In Vitro)

The lipase inhibitory activity of the fat absorption inhibiting agent (C) was evaluated as follows.

Preparation of Enzyme Solution

Five milliliters of 0.1 M citrate buffer solution (pH 6.0) was added to 0.5 g of rat intestinal acetone powder (Sigma-Aldrich Japan G.K). The mixture was agitated on ice for 1 hour, and centrifuged at 4° C. at 10,000 rpm for 45 minutes. The supernatant was diluted to 100-fold in citrate buffer solution to produce an enzyme solution.

Activity Evaluation

The activity of the fat absorption inhibiting agent (C) was evaluated using Lipase Kit S (Pharma Biomedical Co., Ltd.). To a 24-well plate, 100 µL of each of the predetermined concentrations of an aqueous solution of the fat absorption inhibiting agent (C) (sample), 237 µL of a color development reagent solution, 9 µL of the enzyme solution, and 4 µL of an esterase inhibitor were added, and incubated at 30° C. for 5 minutes. Then 25 µL of a substrate solution was added, and the reaction was allowed to proceed at 30° C. for 30 minutes under protection from light. After addition of 700 µL of a reaction stop solution, the absorbance was measured at 412 nm.

Control Evaluation

Wells for control evaluation were prepared on a 24-well plate at the same sample positions. To the plate, 100 µL of each of the predetermined concentrations of an aqueous solution of the fat absorption inhibiting agent (C) (sample), 237 µL of a color development reagent solution, 9 µL of the enzyme solution, and 4 µL of an esterase inhibitor were added, and incubated at 30° C. for 35 minutes under protection from light. After addition of 700 µL of a reaction stop solution and 25 µL of a substrate solution, the absorbance was measured at 412 nm.

Calculation

Blanks were prepared using a solvent alone in place of the aqueous solution of the fat absorption inhibiting agent (C) as a sample. The blanks were also subjected to activity evaluation and control evaluation.

The lipase activity of the sample was calculated by the following calculation formula:

Lipase activity (%)=100×(absorbance of wells for activity evaluation−absorbance of wells for activity evaluation (control))/(absorbance of blanks−absorbance of blanks (control))

Figure 4:
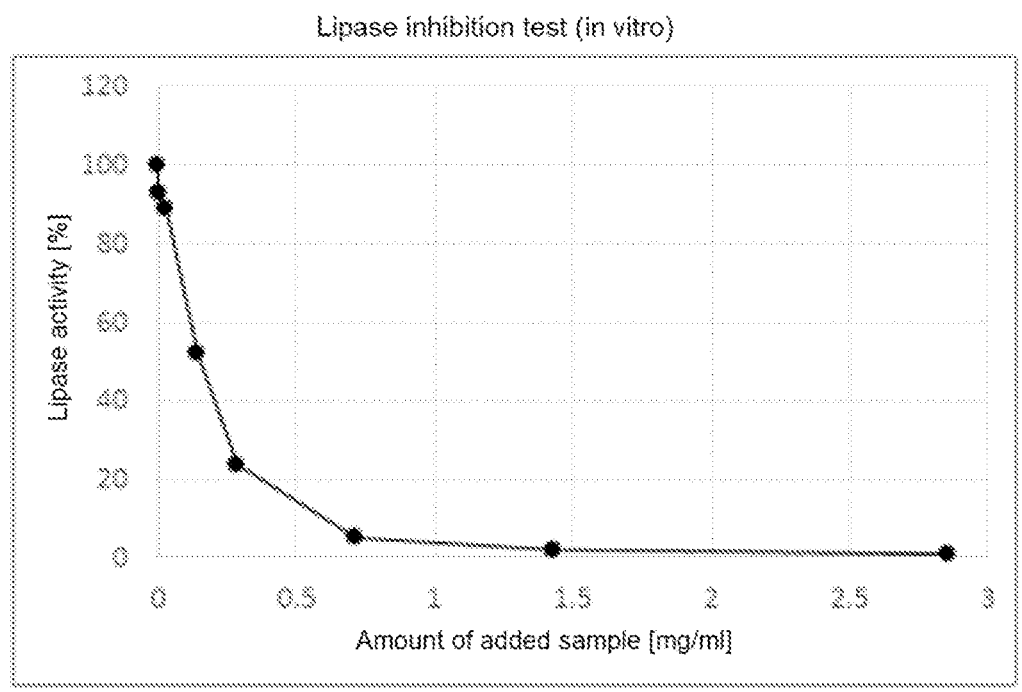
FIG. 4 is a graph showing the results of a lipase inhibition test (in vitro).

The results of Test Example 5 are shown in FIG. 4. The amount of the added sample indicates the final concentration of the fat absorption inhibiting agent (C) in each well. The fat absorption inhibiting agent (C) showed potent lipase inhibitory activity in a dose-dependent manner (the concentration that inhibits 50% of lipase activity ($IC_{50}$)=140 µg/mL).

Test Example 6: Long-Term Ingestion Test (In Vivo)

The fat absorption inhibiting agent was evaluated in a long-term ingestion test (in vivo) as follows.

C57BL/6 mice (male, 5 weeks old) were divided into two groups: a control group and a pulverized defatted sesame seed group (10 animals per group). The control group was fed with free access to a high-fat diet. The pulverized defatted sesame seed group was fed with free access to a high-fat diet mixed with 0.1% by mass (human equivalent dose: about 0.5 g/day) of the pulverized defatted sesame seeds (the fat absorption inhibiting agent (A)) produced in Production Example 1. The body weight was measured every week for 4 weeks.

Figure 5:
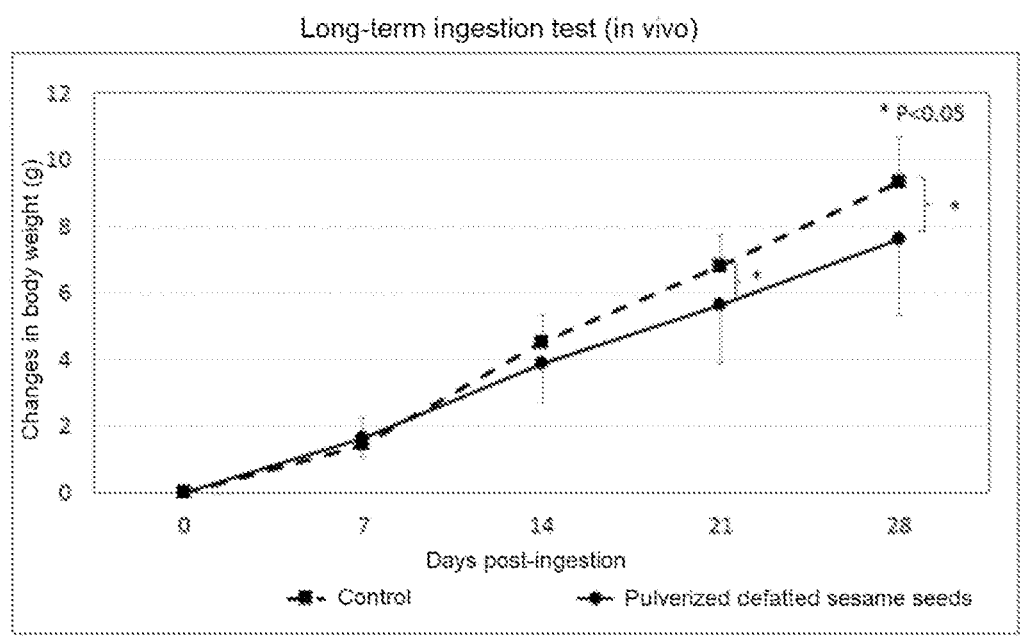
FIG. 5 is a graph showing the results of a long-term ingestion test (in vivo).

The results of Test Example 6 are shown in FIG. 5. The results demonstrate that long-term ingestion of the fat absorption inhibiting agent (A) significantly inhibits increase in the body weight as compared with that of the control group at 21 days (P=0.02) and 28 days (P=0.02) after the ingestion of the agent.

INDUSTRIAL APPLICABILITY

The present invention provides a novel fat absorption inhibiting agent. The fat absorption inhibiting agent of the present invention is produced from a food material, and is therefore highly safe. The fat absorption inhibiting agent of the present invention has excellent fat absorption inhibitory activity and excellent lipase inhibitory activity. The fat absorption inhibiting agent of the present invention is easy to produce without requiring complicated production procedures. The food of the present invention comprises the fat absorption inhibiting agent of the present invention and therefore has fat absorption inhibitory activity and lipase inhibitory activity. The defatted sesame seeds of the present invention can be appropriately used as an ingredient of the fat absorption inhibiting agent of the present invention. The agent, food, and defatted sesame seeds of the present invention can therefore be administered to a human or animal to inhibit obesity of the human or animal. The present invention can be appropriately applied to pharmaceutical products, foods, food additives, functional foods, etc. for treating or preventing obesity, diseases caused by accumulation of fats, such as serum hypertriglyceridemia, or diseases caused by obesity, such as diabetes mellitus, hyperlipemia, hypertension and arteriosclerosis, or for dieting.

The invention claimed is:

1. A method for inhibiting fat absorption in a human or animal, wherein the method comprises administering, to a human or animal, pulverized defatted sesame seeds or a processed product thereof, wherein the pulverized defatted sesame seeds or the processed product thereof inhibit fat absorption in the human or animal and wherein the pulverized defatted sesame seeds or the processed product thereof has a 50th percentile particle size of 1 to 200 μm as determined by laser diffraction/scattering and a compressibility index of 30 to 80%.

2. The method according to claim 1, wherein the pulverized defatted sesame seeds or the processed product thereof has lipase inhibitory activity.

3. The method according to claim 1, wherein the pulverized defatted sesame seeds or the processed product thereof is contained in a food.

4. The method according to claim 2, wherein the pulverized defatted sesame seeds or the processed product thereof is contained in a food.

5. The method according to claim 1, wherein the pulverized defatted sesame seeds or the processed product thereof has lipase inhibitory activity.

6. The method according to claim 1, wherein the pulverized defatted sesame seeds or the processed product thereof is contained in a food.

7. The method according to claim 5, wherein the pulverized defatted sesame seeds or the processed product thereof is contained in a food.

* * * * *